United States Patent [19]
Nishimura

[11] Patent Number: 4,660,551
[45] Date of Patent: Apr. 28, 1987

[54] MEN'S BRIEFS

[76] Inventor: Atsumi Nishimura, 313, Hibaru, Minami-ku, Fukuoka-shi, Fukuoka-ken, Japan

[21] Appl. No.: 716,957

[22] Filed: Mar. 28, 1985

[30] Foreign Application Priority Data

| Apr. 4, 1984 | [JP] | Japan | 59-068073 |
| Oct. 13, 1984 | [JP] | Japan | 59-154925[U] |
| Feb. 2, 1985 | [JP] | Japan | 60-019097 |
| Feb. 2, 1985 | [JP] | Japan | 60-019098 |

[51] Int. Cl.⁴ .......................... A61F 5/00; A41B 9/02
[52] U.S. Cl. .......................................... 128/79; 2/405; 128/159
[58] Field of Search ................... 2/403, 404, 405, 401; 128/79, 159, 158

[56] References Cited

U.S. PATENT DOCUMENTS

| 2,068,173 | 1/1937 | Galves | 128/79 |
| 2,264,934 | 12/1941 | Cronk | 128/158 |
| 3,166,764 | 1/1965 | Stedman et al. | 2/403 |
| 3,459,181 | 8/1969 | Mann | 2/403 X |
| 4,345,337 | 8/1982 | Chung | 2/405 |

FOREIGN PATENT DOCUMENTS

| 280164 | 1/1952 | Switzerland | 2/405 |
| 459968 | 1/1937 | United Kingdom | 2/405 |
| 734394 | 7/1955 | United Kingdom | 128/79 |
| 1035192 | 7/1966 | United Kingdom | 2/405 |

*Primary Examiner*—H. Hampton Hunter
*Attorney, Agent, or Firm*—Jordan and Hamburg

[57] ABSTRACT

Men's briefs capable of holding the penis correctly during the brisk motion of the wearer, eliminating uncomfortable feeling due to sweating in the pelvic region of the wearer, vitalizing the wearer, and giving confident feeling to the wearer. The men's briefs comprise an inner piece superposed over the reverse side of the front part of the main body with the top side and the opposite lateral sides thereof sewn to an elastic waistband and elastic legbands surrounding the leg openings repectively to form a penis receiving part; a penis holding tube made of an elastic material disposed so as to extend from one stitched position where one of the lateral sides of the inner piece is sewn to the elastic legband to the other stitched position where the other lateral side of the inner piece is sewn to the elastic legband, so as to form a penis inserting hole in the lower part of the inner piece; and an urethra pressure preventive member having a V-shaped recess provided in the central portion of the lower part of the penis holding tube.

7 Claims, 17 Drawing Figures

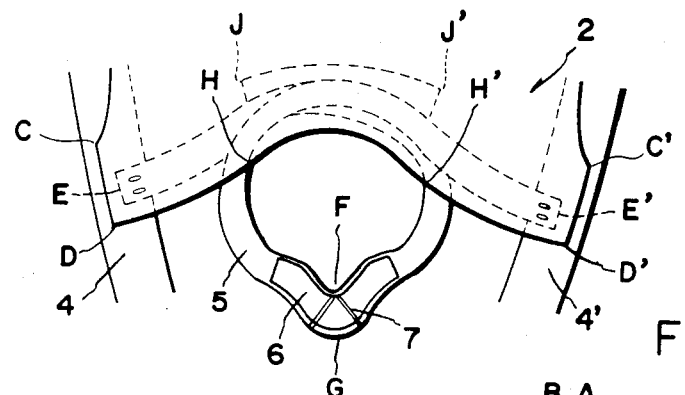
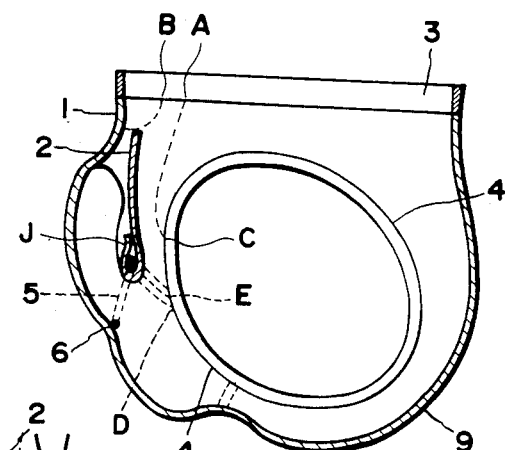
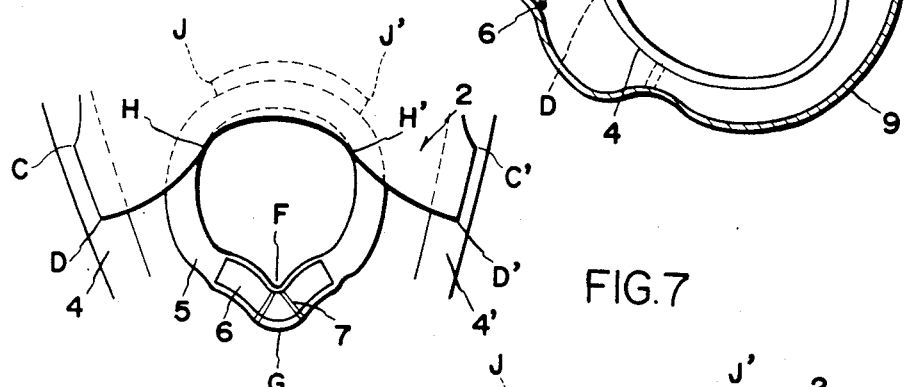
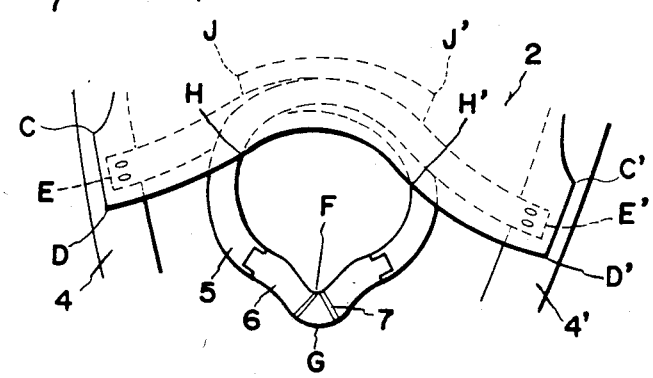

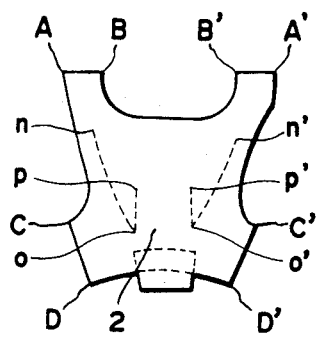
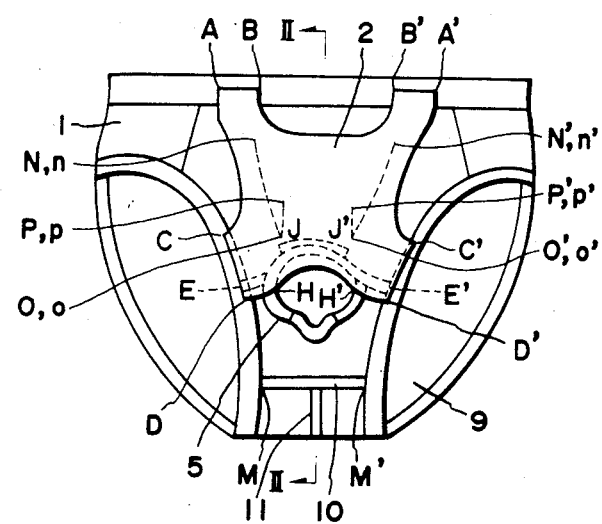
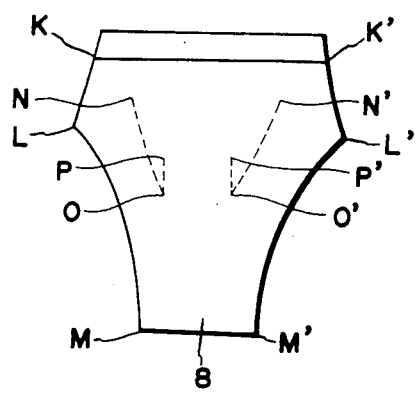
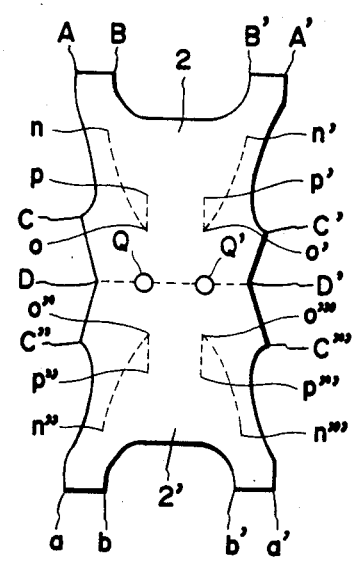
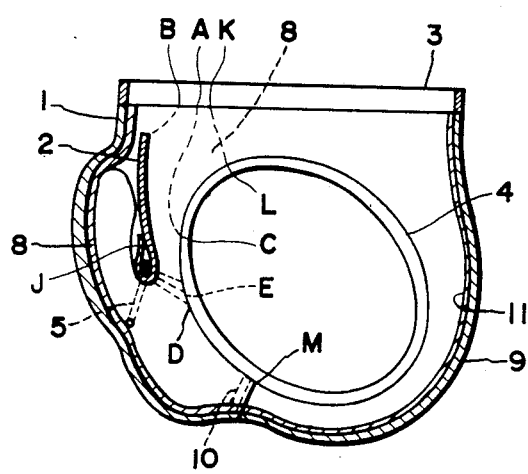

MEN'S BRIEFS

BACKGROUND OF THE INVENTION

1. Field of the Invention

This invention relates to improvement in men's briefs and more particularly to improvements in the structure of the penis holding portion of men's briefs.

2. Description of the Prior Art

Conventional men's underpants are unsatisfactory from the aspect of supporting the sexual organ. Therefore, the leg openings of underpants are loosened by the brisk motion of the body and expose parts of the body which are normally covered, and, in addition, such conventional underpants are unable to overcome uncomfortable friction between the legs particularly when legs are sweaty in hot seasons.

SUMMARY OF THE INVENTION

Accordingly, it is an object of this invention to improve such defects of conventional underpants and to provide men's briefs capable of appropriately holding the sexual organ even during strenuous motion of the body, and eliminating discomfort resulting from sweating, and assuring vigor of the body.

The object of this invention is achieved by men's briefs having a penis holding portion formed from an inner piece and provided with a V-shaped recess in a lower part of a loop-shaped tube surrounding a penis for protecting an urethra from pressure.

The above and other objects, features and advantages of this invention will become more apparent from the following description of the preferred embodiments thereof taken in connection with the accompanying drawings.

BRIEF DESCRIPTION OF THE DRAWINGS

FIG. 4 is an enlarged front view of a penis holding tube employed in the briefs shown in FIG. 3;

FIG. 5 is a sectional view taken along the line I—I of FIG. 3;

FIGS. 6 and 7 show other features of the penis holding tube shown in FIG. 4;

FIG. 8 shows another feature of an inner piece shown in FIG. 2 employed in the second embodiment of this invention;

FIG. 9 is a front view of an intermediate piece to be combined with an inner piece shown in FIG. 8 for forming another feature of the penis holding space in the briefs of this invention;

FIG. 10 is an inside-out view of the briefs provided with the penis holding space by the inner piece shown in FIG. 8 together with the intermediate piece shown in FIG. 9;

FIG. 11 is a sectional view taken along the line II—II of FIG. 10;

FIG. 12 shows another inner piece for forming the penis holding space formed by doubling two inner pieces;

DETAILED DESCRIPTION OF THE PREFERRED EMBODIMENTS

The first embodiment of this invention will be described hereinafter with reference to FIGS. 1 to 5.

Figure 1:
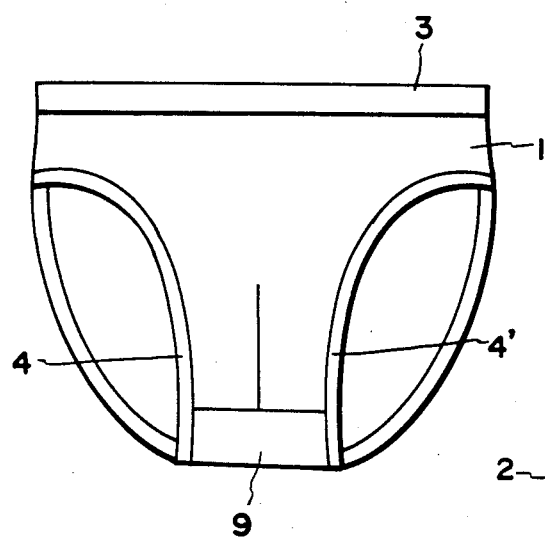
FIG. 1 is a front view of a pair of briefs, in the first embodiment, according to this invention.
Figure 2:
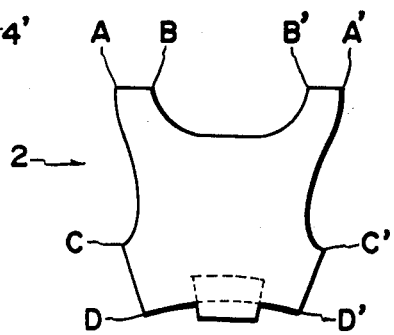
FIG. 2 is a front view of an inner piece which is sewn in the front part of the briefs for forming a penis receiving portion in the briefs shown in FIG. 1.
Figure 3:
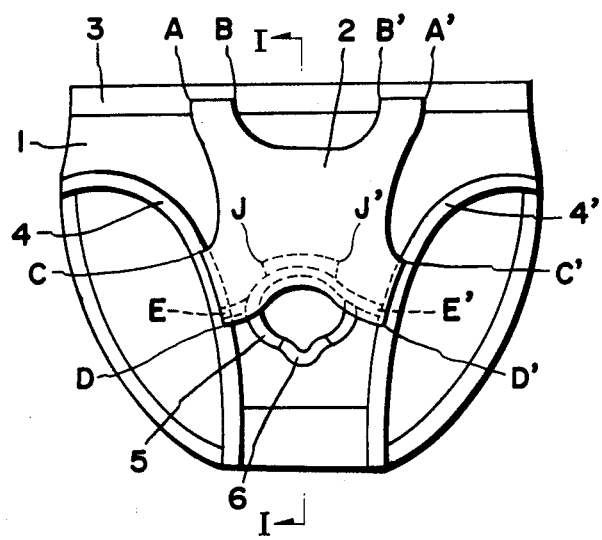
FIG. 3 is an inside-out view of the briefs shown in FIG. 1.

Referring to FIG. 1, an inner piece 2 shown in FIG. 2 is sewn to the inside of the front of a main body 1. The top sides A-B and A'-B' of the inner piece 2 shown in FIG. 2 are sewn to an elastic waistband 3, while the lateral sides C-D and C'-D' of the same are sewn to elastic legbands 4 and 4' surrounding the leg openings respectively, as shown in FIG. 3. Between a stitched position E where the inner piece is stitched to the elastic legband 4 and the other stitched position E' where the inner piece is stitched to the elastic legband 4', an expandable penis holding tube 5 formed in a loop, such as a tubular rubber loop, is disposed so as to surround the root of the penis of the wearer. Tip ends of the penis holding tube 5 are sewn to the elastic legbands 4 and 4' at the stitched positions E and E' respectively so that the penis holding tube 5 will contact the swelled penis moderately by its own expansibility and the internal pressure. In the center of the lower portion of the penis holding tube 5, an urethral pressure preventive member 6 formed, for example, from an aluminum pipe, and having a V-shaped recess F is attached to the penis holding tube 5, to enable urine or sperm to pass through the urethra without hindrance. As shown in FIGS. 4 and 5 the urethra pressure preventive member 6 is sewn to the central portion G of the main body with a thread 7. The lower part of the inner piece 2 is folded back so as to wrap up the central portion H—H' of the penis holding tube 5 and is sewn to the main body 1 at the central part J—J' thereof.

FIG. 6 shows another feature of the penis holding tube 5 shown in FIG. 4. This penis holding tube 5 is sewn in the middle of the space between the stitched positions D and D' where the lateral sides C-D and C'-D' are stitched to the elastic legbands 4 and 4' surrounding the leg opening respectively, so as to surround the root of the penis. The diameter of the penis holding tube 5 is somewhat smaller than that of the erected penis of an adult to cause moderate contact pressure. The bottom portion of said penis holding tube 5 contains an aluminum tube 6 having a V-shaped recess in the center of the lower portion thereof. This aluminum tube 6 is sewn in place with the thread 7 at the position G of the main body 1. The lower portion of the inner piece 2 may be folded back so as to wrap up the central portion H—H' of the penis holding tube 5 and may be sewn to the main body 1 at the positions J and J'.

In the first embodiment shown in FIG. 4, the aluminum urethra pressure preventive member 6 having the V-shaped recess F is provided in the center of the lower portion of the penis holding tube 5 extending between the elastic legbands 4 and 4' so as to surround the root of the penis. The aluminum urethra pressure preventative member 6 may be substituted by a plastic or hard rubber member having a V-shaped recess at its center. This plastic or hard rubber member may be mounted on each end of the penis holding tube 5 and sewn to the central portion G of the main body 1. The lower portion of the inner piece 2 may be folded back so as to wrap up the central portion H—H' of the penis holding tube 5 and may be sewn to the main body 1 at stitched positions J and J'.

Another mode of the inner piece 2 for forming a penis receiving portion is shown in FIGS. 8 to 11. In the above-mentioned first mode of the inner piece 2, as shown in FIG. 3, the lateral sides C-D and C'-D' are sewn to the elastic legbands 4 and 4'. However, to hold the penis correctly in the central portion of the inner piece 2, the inner piece 2 may be stitched on each side with respect to the central portion to the main body 1 along vertical and diagonal lines n-o, o-p, n'-o' and o'-p' in FIG. 8 and to the elastic legbands 4 and 4'. An intermediate piece 8 shown in FIG. 9 is superposed over the inner piece 2 shown in FIG. 8 to form a penis receiving portion between the inner piece 2 and the intermiedate piece 8 as shown in FIGS. 10 and 11. The intermediate piece 8 is placed over the inner surface of the main body 1. The upper side K—K', the opposite lateral sides L'-M and L'-M', and the bottom sides M-M' are sewn to the elastic waistband 3, the elastic legbands 4 and 4', and a rear piece 9, respectively. Furthermore, an elastic band 10 is sewn to the bottom side M—M', the inner piece 2 is superposed over the inner surface of the intermediate piece 8, and the top sides A-B and A'-B', and the lateral sides C-D and C'-D' of the inner piece 2 are sewn to the elastic waistband 3 and the elastic legbands 4 and 4'. The stitch lines n-o-p and n'-o'-p' of the second embodiment of the inner piece are superposed on stitch lines N-O-P and N'-O'-P' of the intermediate piece 8 formed by superposing the inner piece 2 and the intermediate piece 8 and sewing the two together. The lower portion of the inner piece 2 is folded back so as to wrap up the central portion H—H' of a rubber tube or an annular rubber tube for correctly holding the penis at the root thereof in place and sewn to the side J—J' of the intermediate piece 8 to form an enclosure with the top and bottom thereof open.

The above-mentioned penis receiving portion may be provided with a second inner piece 2' in addition to the inner piece 2, to absorb sweat wetting the penis and the abdominal region of the body and to eliminate uncomfortable friction between adjacent parts of the body.

Figure 13:
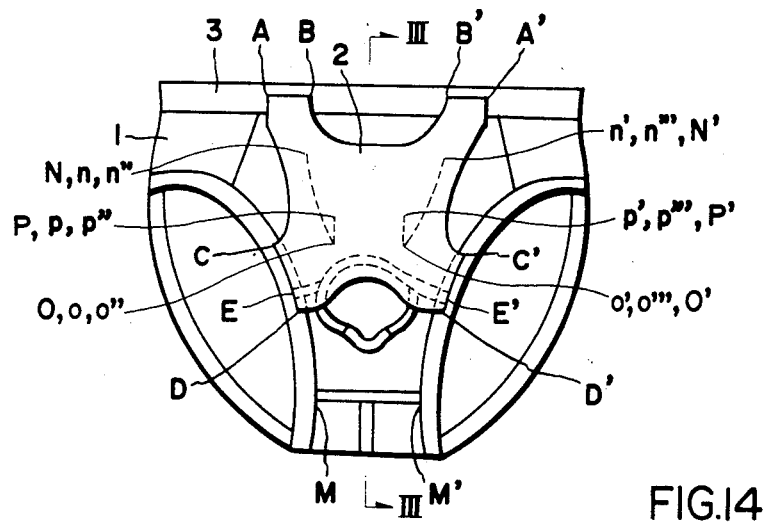
FIG. 13 is an inside-out view of the briefs provided with the penis holding space formed by the intermediate piece together with an inner piece shown in FIG. 12 and the penis holding tube shown in FIG. 7.
Figure 14:
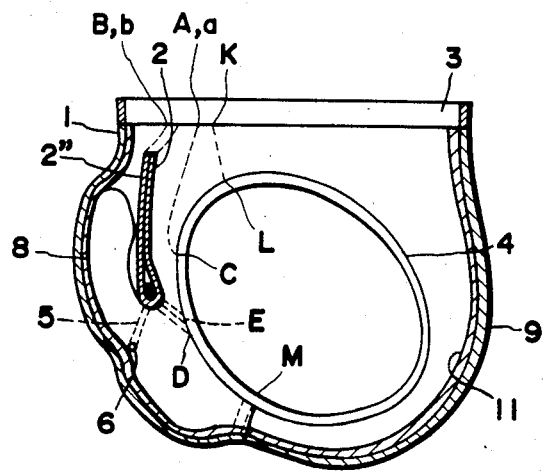
FIG. 14 is a sectional view taken along the line III—III of FIG. 13.

FIGS. 12 to 14 show a mode employing a construction having the above-mentioned functions, Referring to FIGS. 12 to 14, in which the second inner piece 2' in shown, the top side K—K', the opposite lateral sides L—M and L'-M', and the bottom side M—M' of the intermediate piece 8 placed on the inner surface of the main body 1 are sewn to the elastic waistband 3, the elastic legbands 4 and 4' surrounding the leg openings, and the rear piece 9, respectively. The inner piece 2 is placed on the inner surface of the intermediate piece 8 and the top sides A-B and A'-B', and the opposite lateral sides C-D and C'-D' thereof are sewn to the elastic waistband 3 and the elastic legbands 4 and 4' respectively. The inner piece 2 and the second inner piece 2' are formed symmetrically by folding along the line D—D'. The second inner piece 2' is folded back along the folding line D—D' so as to be superposed over the inner surface of the inner piece 2 and so as to wrap up the central position of the penis holding tube 5 along the folding line D—D'. In the central portion of the folding line D—D', small holes Q and Q' are formed to extend the opposite ends of the penis holding tube 5 therethrough to the elastic legbands 4 and 4'. The extremities of the opposite ends of the penis holding tube 5 are sewn to the elastic legbands 4 and 4' at stitched positions E and E', respectively. The vertical and diagonal stitch lines n-o-p and n'-o'-p' formed on opposite sides of the first inner piece to hold the penis therebetween in the intermediate portion between the inner pieces 2 and 2', and the stitch lines n''-o''-p'' and n'''-o'''-p''' of the second inner piece are superposed over the stitch lines N-O-P and N'-O'-P' formed in the intermediate piece 8 by superposing the first inner piece and the intermediate piece. Then, the inner pieces 2 and 2' are sewn together to form an enclosure with its top and bottom open between the intermediate piece 8 and the inner pieces 2 and 2'.

The intermediate piece employed in the abovementioned second mode is provided with an elastic band 10. In a further embodiment, an elastic band 11 may be extended from the central portion of the elastic band 10 through the central portion of the rear side of the briefs to the elastic waistband 3. This elastic band 11 braces and stimulates the hip's center line to brace up the energy.

The penis holding tube 5 shown in each drawing as mentioned above may be provided with a size adjusting member capable of changing the diameter of the penis holding tube in case the diameter of the penis holding tube 5 is too small.

Figure 15:
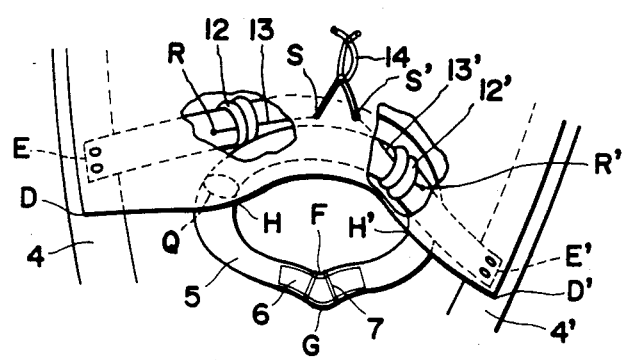
FIG. 15 is a side view showing the details of a pull string for adjusting the inner diameter of the penis holding tube.

FIG. 15 shows a penis holding tube provided with such a size adjusting member. Referring to FIG. 15, the extremities E and E' of the penis holding tube 5 are sewn to the elastic legbands 4 and 4' respectively. The middle portion of the penis holding tube 5 is formed by an urethra pressure preventive member 6 having a V-shaped recess F. The penis holding tube 5 is sewn to the main body 1 in the central portion G with a sewing thread 7. The lower portion of the inner piece 2 is folded back and sewn to the main body 1 at the stitched positions J and J' so as to wrap the penis holding tube 5 along the folding line H—H'. Slip stopping rubber bands 12 and 12' are provided on the expandable penis holding tube 5 in a portion corresponding to the folding line H—H' to allow the adjustment of the size of the expandable penis holding tube 5 and to restrict the expansion or contraction of the expandable penis holding tube 5 after the adjustment of the size. Pull strings 13 and 13' are provided to loosen the expandable penis holding tube 5 in case the penis is oppressed excessively. The pull strings 13 and 13' are connected each at one end to the expandable penis holding tube 5 at the positions R and R' and extended along the backside of the fabric through holes S and S' formed in the central portion of the inner piece. The pull strings 13 and 13' are connected each at their free ends to a pull string 14.

Figure 16:
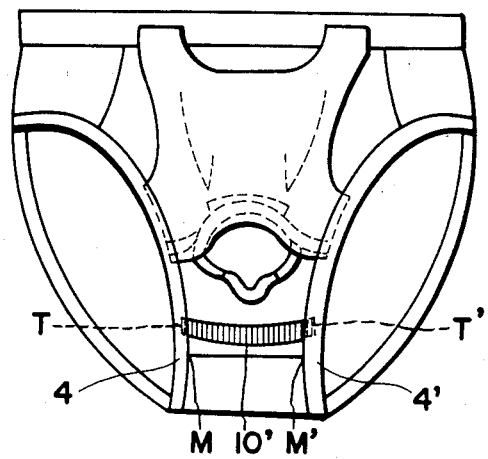
FIGS. 16 and 17 show a modification of the elastic band 10 shown in FIG. 10.
Figure 17:
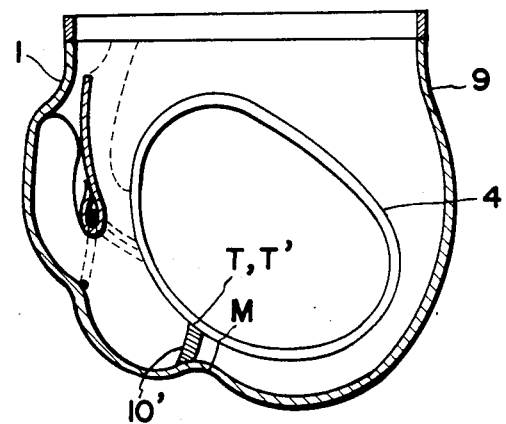

An elastic band 10', as shown in FIGS. 16 and 17, is provided between the elastic legbands 4 and 4' by sewing its both ends with said legbands 4 and 4' at the stitched positions. This elastic band 10' formed from a flat tape bridged over with said legbands 4 and 4' can move and take position appropriately in the intermediate portion while raising it so that the lower part of the testicles can be supported. The opposite ends of the elastic band 10' are sewn to the elastic legbands 4 and 4' surrounding the leg openings respectively at the positions T and T'.

The briefs according to this invention have the following meritorious effects:

(1) Since the briefs have no opening in the front thereof and the penis is held in place, the penis is never exposed.

(2) Since the abdominal region, the penis and the scrotum are separated from each other by the front inner piece and the penis holding tube, uncomfortable friction between the skin of the adjacent parts of the body is obviated even when the skin is wetted with sweat, thereby improving the comfort of the wearer.

(3) In case the wearer tumbles down to the ground during motion, such as while participating in sports, the penis is protected from abrasions by double layers of fabric and held firmly in place.

(4) Recently trousers are tailored tightly, therefore the penis is pulled out upward in most cases for urination. Since the briefs according to this invention have an opening in the upper portion thereof, the wearer is allowed to urinate without hindrance.

(5) The size of the penis holding tube can be adjusting according to the size of the penis of the wearer and is capable of varying in size in accordance with the variation of the size of the penis.

(6) Since men's pelvic region is always braced, the wearer tends to feel more energetic and confident.

(7) Since the penis holding tube contains a solid recessed member in the central portion thereof, in the portion corresponding to the urethra, an urethra pressure preventive member having a V-shaped recess, even if the penis swells due to the urgency of urination, the wearer is allowed to urinate without any hindrance.

What is claimed is:

1. Men's briefs comprising a main body having a front part and a rear part, said front part and said rear part each having an upper end formed as an elastic waistband, leg openings in at least portions of each of said front and rear parts, an inner piece superimposed over an inside of said front part, securing means securing said inner piece to said body, said inner piece along with said front part defining a penis-receiving part, a penis-holding tube made of an elastic material, said tube being disposed as a loop to form a compressing tube for surrounding a penis root at a lower part of said inner piece, said compressing tube being provided with a size adjusting member comprising pull string means connected at one end to the compressing tube and extended along the back of said body through holes formed in the central portion of said inner piece, said pull string means being adjustable for loosening the compressing tube in emergencies when pain is caused by sudden fastening of the loop.

2. Men's briefs comprising a main body having a front piece and a rear piece, said front piece and rear piece each having a top connected to a waistband and two lower parts each connected to a legband, said front piece having an inner surface surface and an outer surface, an inner piece superimposed over the inner surface of said front piece and attached to the waistband and two leg bands for accommodating a penis between said front piece and said inner piece, said inner piece having a lower part and said front piece having a lower central part, a loop-shaped penis-holding rubber tube having ends attached to the legbands, a bottom of center part of said tube being attached to the lower central part of said front piece and said tube having an adjustable middle part, the lower part of said inner piece being folded up and secured to itself to form a passage accommodating the adjustable middle part of the loop-shaped penis-holding rubber tube therein, and means connected to the adjustable middle part of the loop-shaped penis-holding rubber tube for manually adjusting the adjustable middle part to vary the size of a loop formed by the loop-shaped penis-holding rubber tube to any penis size.

3. Men's briefs according to claim 2, further comprising an intermediate piece between the front piece of the main body and the inner piece defining a penis-receiving portion between the intermediate piece and the inner piece, the intermediate piece having lateral sides and the inner piece having lateral sides, the lateral sides of the intermediate piece and the inner piece being joined together to form a penis-receiving pocket, the penis-receiving pocket having open top and bottom sides for holding the penis in an upright position.

4. Men's briefs according claim 3 further comprising a second inner piece having a same shape as the first said inner piece and formed integrally with the first said inner piece and symmetrically with the first said inner piece with respect to a folding line, the second inner piece having a lower part folded along said folding line to form said passage for accommodating the adjustable middle part of the loop-shaped penis-holding rubber tube.

5. Men's briefs according to claim 3 further comprising an elastic band connected to and extending from the lower central part of said front piece across and up said rear piece to the waistband for bracing and stimulating a hip's central line.

6. Men's briefs according to claim 3 further comprising an urethra pressure-preventive member having a central V-shaped metallic recess provided in the bottom center part of the loop-shaped penis-holding rubber tube.

7. Men's briefs according to claim 6, wherein said urethra pressure-preventive member is formed separately from said penis-holding tube and has opposite ends thereof fitted on said penis-holding tube.

* * * * *